US012765927B2

(12) United States Patent
Sylvestre et al.

(10) Patent No.: US 12,765,927 B2
(45) Date of Patent: Oct. 20, 2026

(54) FEMUR PLATE

(71) Applicant: Stryker European Operations Holdings LLC, Portage, MI (US)

(72) Inventors: Pierre-Luc Sylvestre, Grenchen (CH); Andreas Wiederkehr, Biel/Bienne (CH); Emil Schemitsch, Thornhill (CA); Nicholas D. Morfing, Washingtonville, NY (US); Michael McKee, Paradise Valley, AZ (US)

(73) Assignee: Stryker European Operations Holdings LLC, Portage, MI (US)

( * ) Notice: Subject to any disclaimer, the term of this patent is extended or adjusted under 35 U.S.C. 154(b) by 2 days.

(21) Appl. No.: 18/977,482

(22) Filed: Dec. 11, 2024

(65) Prior Publication Data

US 2025/0099147 A1 Mar. 27, 2025

Related U.S. Application Data

(60) Continuation of application No. 18/118,354, filed on Mar. 7, 2023, now Pat. No. 12,201,334, which is a
(Continued)

(30) Foreign Application Priority Data

Aug. 14, 2017 (EP) .................................... 17001395

(51) Int. Cl.
*A61B 17/80* (2006.01)
*A61B 17/74* (2006.01)
(Continued)

(52) U.S. Cl.
CPC ........ *A61B 17/8061* (2013.01); *A61B 17/742* (2013.01); *A61B 17/744* (2013.01);
(Continued)

(58) Field of Classification Search
CPC . A61B 17/80; A61B 17/8061; A61B 17/8066; A61B 17/8014; A61B 17/8052;
(Continued)

(56) References Cited

U.S. PATENT DOCUMENTS

| | | | |
|---|---|---|---|
| 3,463,148 A | 8/1969 | Treace | |
| 5,607,430 A | 3/1997 | Bailey | |

(Continued)

FOREIGN PATENT DOCUMENTS

| | | | |
|---|---|---|---|
| WO | 96/09012 A1 | 3/1996 | |
| WO | 2004107957 A2 | 12/2004 | |
| WO | 2011003494 A1 | 1/2011 | |

OTHER PUBLICATIONS

Extended European Search Report including Written Opinion for Application No. EP17001395.7 dated Apr. 26, 2018.

*Primary Examiner* — Matthew J Lawson
(74) *Attorney, Agent, or Firm* — Lerner David LLP

(57) ABSTRACT

A femur plate is provided, the femur plate comprising a first end portion anatomically pre-formed to conform to a trochanter region of the femur and a second end portion anatomically pre-formed to conform to a condyle region of the femur, wherein the second end portion comprises at least one first opening configured to receive a bone fastener. The femur plate further comprises an elongate shaft extending from the first end portion to the second end portion, the elongate shaft comprising at least one second opening configured to receive a bone fastener. Furthermore, a periprosthetic implant system comprising the femur plate and a method of implanting the femur plate are provided.

24 Claims, 6 Drawing Sheets

Related U.S. Application Data continuation of application No. 16/906,026, filed on Jun. 19, 2020, now Pat. No. 11,622,799, which is a division of application No. 16/056,813, filed on Aug. 7, 2018, now Pat. No. 10,729,479.

(51) Int. Cl.

| | |
|---|---|
| ***A61B 17/86*** | (2006.01) |
| ***A61F 2/30*** | (2006.01) |
| ***A61F 2/36*** | (2006.01) |
| ***A61F 2/38*** | (2006.01) |

(52) U.S. Cl.

CPC .......... *A61B 17/746* (2013.01); *A61B 17/809* (2013.01); *A61F 2/36* (2013.01); *A61F 2/3609* (2013.01); *A61F 2/3859* (2013.01); *A61B 17/8057* (2013.01); *A61B 17/8066* (2013.01); *A61B 17/86* (2013.01); *A61F 2002/3069* (2013.01)

(58) Field of Classification Search

CPC ..... A61B 17/8057; A61B 17/42; A61B 17/44; A61B 17/809

See application file for complete search history.

(56) References Cited

U.S. PATENT DOCUMENTS

| | | | | |
|---|---|---|---|---|
| 8,267,972 | B1 * | 9/2012 | Gehlert | A61B 17/8014 606/280 |
| 9,668,794 | B2 | 6/2017 | Kuster et al. | |
| 10,058,363 | B2 | 8/2018 | Burke et al. | |
| 11,096,730 | B2 | 8/2021 | Tiongson et al. | |
| 2002/0156474 | A1 | 10/2002 | Wack et al. | |
| 2004/0087954 | A1 | 5/2004 | Allen et al. | |
| 2004/0092935 | A1 | 5/2004 | Manderson | |
| 2006/0058795 | A1 | 3/2006 | Boyd | |
| 2006/0173458 | A1 * | 8/2006 | Forstein | A61B 17/1728 606/281 |
| 2006/0276896 | A1 | 12/2006 | Fallin et al. | |
| 2009/0177240 | A1 | 7/2009 | Perez | |
| 2009/0287215 | A1 * | 11/2009 | Fisher | A61B 17/82 606/280 |
| 2009/0312758 | A1 | 12/2009 | Petit et al. | |
| 2010/0137314 | A1 | 6/2010 | Natsuhara et al. | |
| 2011/0004252 | A1 * | 1/2011 | Velikov | A61B 17/80 606/280 |
| 2011/0112538 | A1 | 5/2011 | Dell'Oca | |
| 2011/0137314 | A1 * | 6/2011 | Kuster | A61B 17/74 606/281 |
| 2011/0166573 | A1 | 7/2011 | Wenk et al. | |
| 2011/0264095 | A1 * | 10/2011 | Cheng | A61B 17/80 606/71 |
| 2011/0313422 | A1 * | 12/2011 | Schwager | A61B 17/8057 606/71 |
| 2012/0016366 | A1 | 1/2012 | Eglseder | |
| 2012/0209270 | A1 | 8/2012 | Segina et al. | |
| 2014/0243907 | A1 | 8/2014 | Cavallazzi et al. | |
| 2014/0336713 | A1 | 11/2014 | Kuster et al. | |
| 2015/0005831 | A1 | 1/2015 | Sands | |
| 2015/0157373 | A1 | 6/2015 | Wolf et al. | |
| 2017/0265915 | A1 | 9/2017 | Langdale et al. | |
| 2018/0036049 | A1 | 2/2018 | Kobayashi | |
| 2018/0256221 | A1 * | 9/2018 | Koay | A61B 17/74 |
| 2019/0269446 | A1 | 9/2019 | Laird | |
| 2023/0058351 | A1 * | 2/2023 | Perez | A61B 17/8057 |
| 2024/0148420 | A1 * | 5/2024 | Tiongson | A61B 17/86 |
| 2024/0277388 | A1 * | 8/2024 | Haidukewych | A61B 17/7233 |
| 2025/0090207 | A1 * | 3/2025 | Machamer | A61B 17/1725 |

* cited by examiner

FEMUR PLATE

CROSS-REFERENCE TO RELATED APPLICATIONS

The present application is a continuation of U.S. patent application Ser. No. 18/118,354 filed Mar. 7, 2023, which is a continuation of U.S. patent application Ser. No. 16/906,026 filed Jun. 19, 2020, now U.S. Pat. No. 11,622,799, which is a continuation of U.S. patent application Ser. No. 16/056,813 filed Aug. 7, 2018, now U.S. Pat. No. 10,729,479, which claims priority from EP patent application Ser. No. 17/001,395.7 filed Aug. 14, 2017, now EP U.S. Pat. No. 3,443,918, the disclosures of which are hereby incorporated herein by reference.

TECHNICAL FIELD

The present disclosure generally relates to a femur plate. In particular, a femur plate to extend from a trochanter region to a condyle region of the femur and a method for implanting the same are described.

BACKGROUND

To promote the healing process of a damaged or fragmented bone, bone plates are commonly attached to an outside surface of the bone. The bone plates act as stabilizing elements for the damaged areas. In addition, they may help to position fragmented bone sections relative to one another.

In case of fractures of long bones, such as the femur, current bone plating systems typically provide stabilizing and fixation for a dedicated region of the bone. For example, a trochanter (i.e., proximal) region or a condyle (i.e., distal) region of the femur is plated.

There is a need for a femur plate and a method of implanting the same that enable a more efficient treatment in certain surgical situations.

SUMMARY OF THE INVENTION

According to one aspect, a femur plate is provided that comprises a first end portion anatomically pre-formed to conform to a trochanter region of the femur and a second end portion anatomically pre-formed to conform to a condyle region of the femur. The second end portion comprises at least one first opening configured to receive a bone fastener. The femur plate further comprises an elongate shaft extending from the first end portion to the second end portion, the elongate shaft comprising at least one second opening configured to receive a bone fastener.

The first end portion and the second end portion of the femur plate may be anatomically pre-formed by bending. The bending may generally result in a curved (e.g., at least partially convex or concave) shape of the corresponding end portion. The pre-forming may be based on average dimensions and shapes of at least the femur trochanter region and femur condyle region, in particular a medial condyle region. The anatomically pre-formed first end portion may be configured to rest in an implanted state against (e.g., to adjoin) the trochanter region of the femur. The anatomically pre-formed second end portion may be configured to rest in an implanted state against (e.g., to adjoin) the condyle region of the femur. One or both of the anatomically pre-formed first and second end portions may be pre-formed in three dimensions (e.g., by having one of a generally concave, convex or concavo-convex shape).

The at least one first and/or second opening may be formed as a through-hole for a bone fastener (e.g., a bone screw). The at least one first and/or second opening may include a counterbore or countersunk portion for receiving a bone fastener head. The femur plate may in an implanted state have a bone facing (e.g., bone contacting) plate surface and an upper plate surface (being arranged substantially opposite to and facing away from the bone facing plate surface). The at least one first and/or second opening may be configured to receive the bone fastener from the upper plate surface towards the bone to be treated. For doing so, at least one of the one or more first and/or second openings may extend transversely to an adjacent region upper plate surface and the bone facing plate surface.

The first end portion of the femur plate may comprise a tapering tip that extends upwardly (e.g., in a vertical direction from the bone facing plate surface to the upper plate surface) from the elongate shaft to conform to the trochanter region. A lateral shape of the first end portion may be substantially axisymmetric to a longitudinal axis thereof. The lateral shape of that first end portion may be substantially tongue-shaped. An angle between the longitudinal axis of the upwardly directed first end portion (e.g., of the tip) and a longitudinal axis of a shaft region adjacent to that first end portion may range between about 15° and about 30°, such as between about 19° and about 24°.

At least one third opening (e.g., extending through the bone facing plate surface and the upper plate surface) may be arranged in the first end portion of the femur plate to receive a bone fastener for insertion into a femur neck and, optionally, up into a femur head. The third opening may be centrally located in the tip of the first end portion.

The first and second openings and the optional third opening located in the femur plate may generally have a similar configuration or may differ from one another, in particular with regard to their orientations relative to the bone facing plate surface and the upper plate surface. One or more of the first and second openings and the optional third opening located in the femur plate may be threaded or comprise other locking structures (e.g., for receiving locking screws). Additionally, or in the alternative, one or more of the first and second openings and the optional third opening located in the femur plate may be non-threaded (e.g., for receiving compressions screws).

In addition or as an alternative to the third opening, the first end portion may comprise a hook or spike configured to be inserted into trochanter bone. The hook may, for example, be formed as a convex-shaped proximal extension of the tapering tip. The spike may, for example, extend from a bone facing surface of the first end portion.

One or both of the first end portion and the second end portion may have a substantially constant thickness. Also the femur plate as a whole may have a substantially constant plate thickness.

In one example, the first end portion comprises at least one channel configured to receive a surgical cable. The channel may be circumferentially closed (e.g., in the form of a bore) or may have an open side (e.g., in the form of a groove). The channel may in particular be open on a bone facing surface of the first end portion. Alternatively, or a second channel, may be open on an upper surface of the first end. The at least one channel may extend generally perpendicular to the longitudinal axis of the first end portion. A plurality of channels may extend substantially parallel to each other.

The surgical cable received in the at least one channel may be used for fixation of the femur plate to the femur or for fixation of another bone plate (arranged, e.g., on the opposite side of the femur plate) to the femur. In this case, the plate thickness may be reduced in the region of the channel.

Multiple first openings may be arranged in the second end portion of the femur plate to each receive a bone fastener for insertion into a medial condyle. The centers of the multiple first openings may generally lie on an oval (e.g., a circle or an egg-shaped form).

The second end portion of the femur plate may be club-shaped. For example, a lateral extension of the second end portion may asymmetrically increase toward the distal end thereof. The second end portion of the femur plate (e.g., the longitudinal axis thereof) may be angled laterally relative to a longitudinal axis of the elongate shaft towards the medial condyle. In particular, an angle between the longitudinal axis of the second end portion and the longitudinal axis of the elongate shaft may range between about 20° and about 80°, such as between about 55° and about 61°.

The elongate shaft of the femur plate may be provided to have a first shaft region and a second shaft region. In one example, the first shaft region is arranged between the first end portion and the second shaft region. Further, at least one of the first shaft region and the second shaft region may be provided with at least one second opening. In this case, the at least one second opening may be arranged to receive bone fasteners for at least one of mono-cortical and bi-cortical fixation.

Bone fasteners can, for example, include locking bone screws, non-locking bone screws (e.g., compression or cortical screws) and bone pegs having rod-like or pin-like shafts.

The first shaft region may be provided with a (first) center line. Centers of two second openings in the first shaft region may optionally lie on opposing sides of that first center line. Further, the centers of the two second openings in the first shaft region may lie on a first (transverse) line intersecting the first center line at an angle of approximately 90° (e.g., at angle of between 85° and 95°). In this case, the first center line may intersect the first transverse line substantially centrally between the centers of the opposing second openings.

In one example, the first shaft region comprises four second openings. In this case, the centers of those four second openings may define a rectangle that is intersected by the first center line of the first shaft region. For example, the first center line runs along the middle axis of the rectangle.

Also, the second shaft region may be provided with a (second) center line. Centers of two second openings in the second shaft region may lie optionally on opposing sides of that second center line. In one example, the two second openings on opposing sides of the second center line are not centered on a second (transverse) line intersecting that second center line at an angle of approximately 90°. At least in this case, two (or more) second openings may lie in a staggered (or zig-zag) manner along the second center line of the second shaft region.

In case of both, the first shaft region and the second shaft region having two second openings, a first average distance of the second openings in the first shaft region to the first center line may be larger than a second average distance of the second openings in the second shaft region to the second center line. In general, a plurality of second openings may substantially be similar or differ from one another, in particular with regard to their sizes and/or shapes. In one example, at least one second opening in an implanted state of the femur plate runs obliquely from the upper plate surface to the bone facing plate surface towards the bone to be treated (such as towards a patient knee).

In addition to the second shaft region, the elongate shaft of the femur plate may comprise a third shaft region being arranged between the second shaft region and the second end portion of the femur plate. In this case, at least one oblique second opening may be located in the third shaft region. In particular, the third shaft region may comprise a (third) center line and the at least one oblique second opening may have a center that lies on that third center line. A plurality of oblique second openings may be provided in the third shaft region so that the centers of the second openings lie in a row along the third center line. Additionally, or alternatively, two oblique second openings may be provided in the third shaft region so that the centers of those second openings lie on opposing sides of the center line of the third shaft region.

At least one of the first center line, the second center line and the third center line may be curved. The second shaft region and at least one of the first shaft region and the third shaft region may extend along a common center line.

Furthermore, the femur plate may comprise at least one of a first elongate hole extending along the first center line in a portion of the first shaft region that faces the second shaft region and a second elongate hole extending along the third center line in a portion of the third shaft region that faces the second shaft region. The first elongate hole and/or the second elongate hole may be provided for receiving means for movably pre-fixing the femur plate to the bone (e.g., to a diaphysis region or a metaphysis region of the femur). An extension of the first elongate hole and/or the second elongate hole along the respective center line may be equal to or larger than an upper plate surface diameter of first substantially circular openings and/or second substantially circular openings.

At least one of the at least one third opening, the at least one first opening and the at least one second opening may comprise a locking structure for locking a bone fastener received through that opening at a selected angle to the femur plate. The locking structure can include a threaded portion or a circumferential lip (or other structure) adapted to lockingly engage the bone fastener, in particular a threaded head thereof. In one variant, the locking structure has one or more protrusions extending in a radial direction towards the plate opening.

A bone fastener can be polyaxially or monoaxially insertable through the plate opening, such that the locking structure may receive a head portion of a bone fastener for locking engagement. A bone fastener may have a self-cutting portion that can be inserted into the plate opening for engaging the locking structure.

According to a further aspect, a periprosthetic implant system is provided that comprises the femur plate presented herein and at least one implant (e.g., a hip prosthesis, a knee prosthesis or an intramedullary nail) configured to be implanted in a region of one of the trochanter and the condyle. At least one of the at least one third opening, the at least one first opening and the at least one second opening of the femur plate may be arranged such that a bone fastener inserted through that opening does not touch the implant in its implanted state. For this purpose, selectable angles for a particular plate opening define a cone that does not coincide with the implant in its implanted state. An opening angle of the cone assumes, for example, values between about 10° and about 50°, especially between about 30° and about 40°. A central axis of the cone may be defined by a vertical extension of the plate opening.

According to a further aspect, there is provided a method of implanting a femur plate, such as the above described femur plate. The method comprises the steps of applying a first end portion of the femur plate to a trochanter region of the femur, attaching a second end portion of the femur plate to a condyle region of the femur by inserting a second bone fastener through a first opening in the second end portion, and attaching an elongate shaft extending from the first end portion to the second end portion to bone by inserting a third bone fastener through a second opening in the elongate shaft. The step of applying the first end portion to the trochanter region may comprise inserting a first bone fastener through a third opening in the first end portion. In addition, or as an alternative to this, the step of applying the first end portion to the trochanter region may comprise inserting a hook or a spike to the trochanter region.

The method may additionally comprise the steps of implanting a prosthesis (e.g., an endoprothesis) in a region of the femur and manipulating at least one of the first bone fastener, the second bone fastener and the third bone fastener, when inserted through an associated opening in the femur plate, to push the prosthesis in an anatomic position. In this context, the bone fasteners may be configured according to the above discussed aspects. The same applies to the prosthesis that may, for example, include a hip prosthesis, knee prosthesis and/or an intramedullary nail.

BRIEF DESCRIPTION OF THE DRAWINGS

Further details, advantages and aspects of the present disclosure will become apparent from the following embodiments taken in conjunction with the drawings, wherein.

DETAILED DESCRIPTION

Figure 1A:
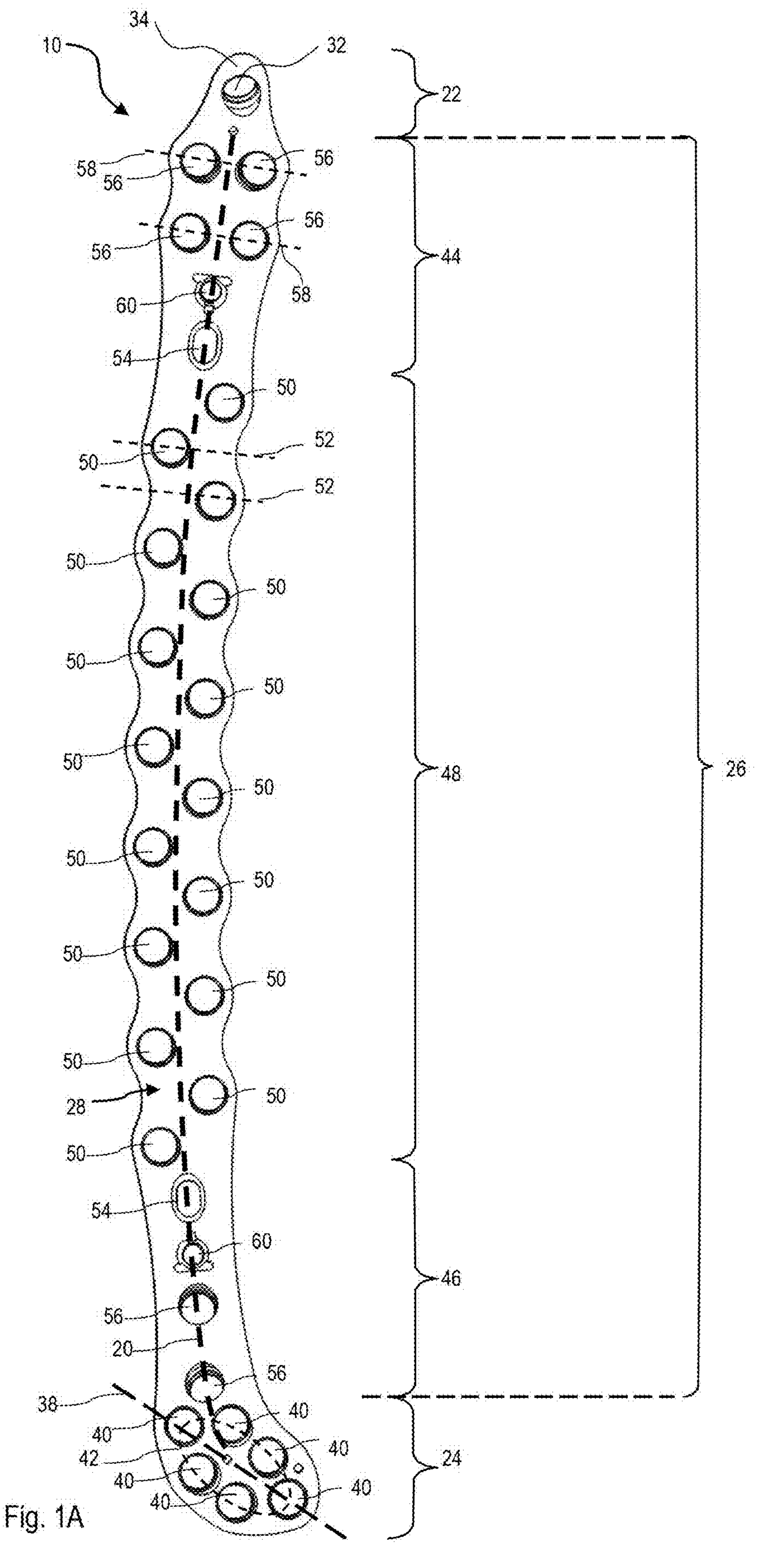
FIG. 1A-1C show a perspective view of a femur plate according to a first embodiment.

In the following, embodiments of a femur plate will be described. The same reference numerals will be used to denote the same or similar structural features.

Figure 1B:
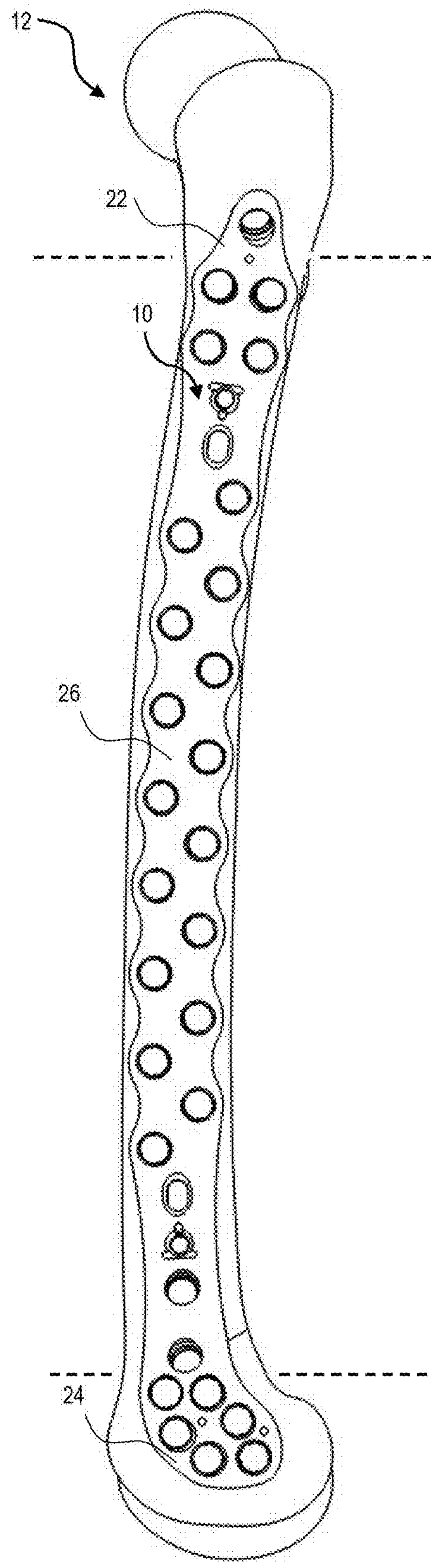
Figure 1C:
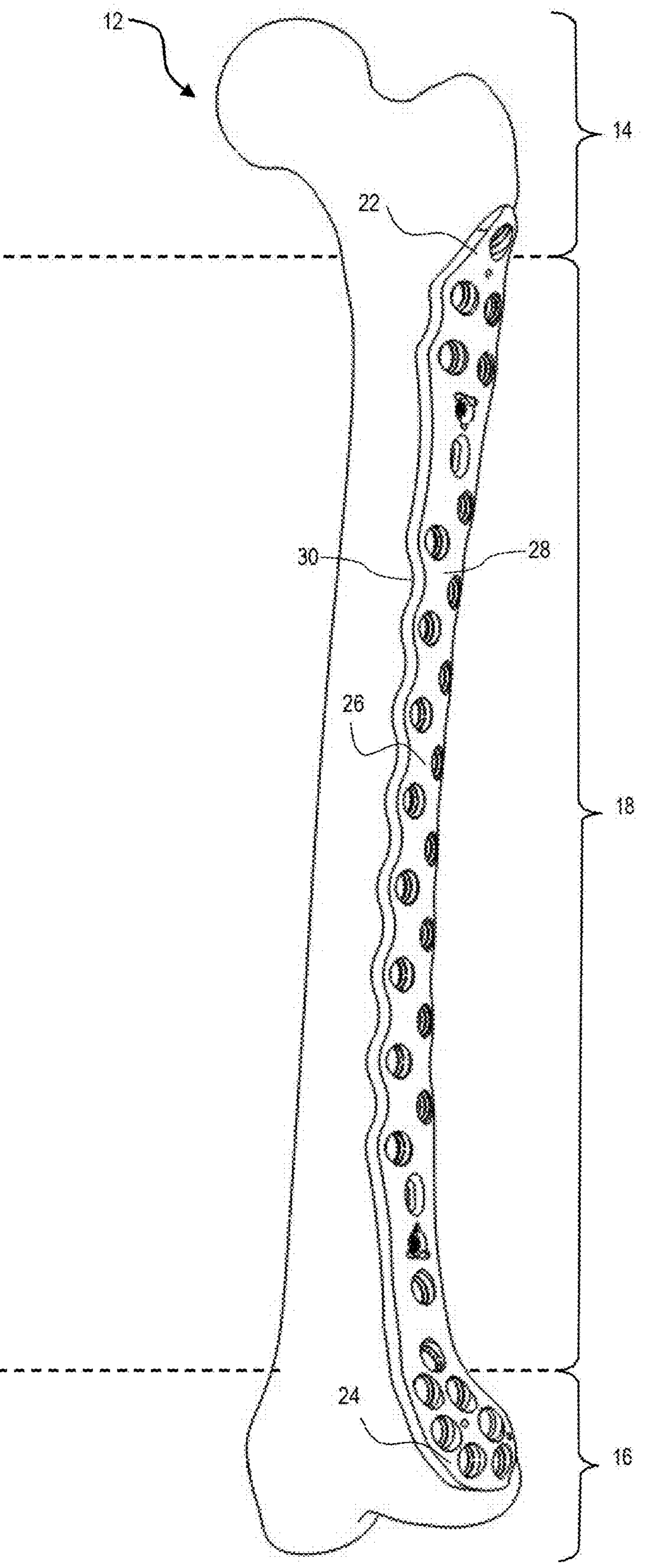

FIGS. 1A to 1C show a perspective view of a femur plate, generally denoted as 10, according to a first embodiment. More specifically, FIGS. 1B and 1C show different perspective views of the femur plate 10 arranged on a left femur, generally denoted as 12, before insertion of bone fasteners, while FIG. 1A shows the femur plate 10 in its non-implanted state. As can be seen from FIGS. 1B and 1C, the femur plate 10 is generally configured to project from a trochanter region 14 to a condyle region 16 of the femur 12, thereby covering a shaft region 18 (i.e., diaphysis and metaphysis regions).

The femur plate 10 is generally configured as an elongated member extending longitudinally along a (imagined) curved center line (see the dotted line denoted as 20 in FIG. 1A). The femur plate 10 comprises a proximal plate portion 22 (a first end portion in a proximal to distal direction), a distal plate portion 24 (a second end portion in the proximal to distal direction) and a shaft portion 26 connecting the proximal plate portion 22 with the distal plate portion 24. FIG. 1A shows a view on an upper surface 28 of the femur plate 10 which, in an implanted state, is substantially opposite to and facing away from a bone facing plate surface 30 (see FIG. 1C).

The femur plate 10 is formed from a single piece of rigid material, such as stainless steel or titanium. In the embodiment shown in FIGS. 1A to 1C, the femur plate 10 further has a substantially constant plate thickness. In another embodiment, the plate thickness may vary along the longitudinal extension of the femur plate 10, such as in regions of a channel for accommodating a surgical cable (see also with regard to FIG. 3C below).

The proximal plate portion 22 according to the embodiment of the femur plate 10 shown in FIGS. 1A to 1C has one opening 32 (that is optional). The proximal plate opening 32 forms a through-hole extending from the upper plate surface 28 to the bone facing plate surface 30. In particular, a vertical extension of the through-hole 32 runs obliquely from the upper plate surface 28 to the bone facing plate surface 30. The through-hole 32 is shaped to have a circular cross-section with a diameter of between about 2 mm and about 10 mm, such as 5 mm.

The proximal plate opening 32 is centrally located in a tapering proximal end portion of the proximal plate portion 22. The proximal end portion has a rounded tip 34. Starting from the tip 34, a lateral extension of the proximal plate portion 22 gradually enlarges distally toward the shaft region 26. In particular, the lateral shape of the proximal plate portion 22 shown in FIGS. 1A to 1C is substantially axisymmetric to a (not-shown) longitudinal axis of the proximal plate portion 22. For example, the proximal plate portion 22 is generally tongue-shaped.

In another embodiment of the femur plate 10, the proximal plate portion 22 may have no opening or a plurality of openings 32. The plurality of openings 32 may generally be similar to or may at least partially differ from the proximal plate through-hole 32. Further, one or more openings 32 in the proximal plate portion 22 may run orthogonally from the upper plate portion 28 to the bone facing plate portion 30. At least in the case of a plurality of proximal plate openings 32, the proximal plate portion 22 may have a different (e.g., asymmetric) shape, such as a club-shape.

The distal plate portion 24 according to the femur plate 10 shown in FIGS. 1A to 1C is generally club-shaped. In particular, a lateral extension of the distal plate portion 24 increases asymmetrically toward the distal end of the femur plate 10. Further, a longitudinal axis (indicated by the dash\dotted line 38 shown in FIG. 1A) of the distal plate portion 24 is angled with regard to a (not-shown) average longitudinal axis of the shaft portion 26. For example, a lateral angle of between about 55° and about 61° between the longitudinal axis 38 of the distal plate portion 24 and the longitudinal axis of the shaft portion 26 is provided.

The distal plate portion 24 comprises a total of six openings 40. The distal plate openings 40 form through-holes extending from the upper plate surface 28 to the bone facing plate surface 30 of the femur plate 10. In the embodiment shown in FIGS. 1A to 1C, the distal plate through-holes 40 substantially correspond in size and shape to the proximal plate through-hole 32 in the proximal plate portion 22. Further, the distal plate through-holes 40 run obliquely from the upper plate surface 28 to the bone facing plate surface 30.

The distal plate openings 40 are arranged in the distal plate portion 24 such that their centers substantially lie on an egg-shaped oval (indicated by the dashed oval 42 shown in FIG. 1A) on the upper plate surface 28. For example, a symmetry axis of the oval 42 coincides with the longitudinal axis 38 of the distal plate portion 24. In another embodiment, the distal plate portion 24 may have a different number of openings 40 and/or a different arrangement of the openings 40. For example, a plurality of (e.g., three) openings 40, such as the distal plate through-holes 40 shown in FIGS. 1A to 1C, may be arranged in a row such that their centers lie along an axis substantially coinciding with the longitudinal axis 38 of the distal plate portion 24.

The elongated shaft portion 26 of the embodiment of the femur plate 10 shown in FIGS. 1A to 1C comprises a proximal shaft region 44 (a "first" shaft region in the proximal to distal direction) facing the proximal plate portion 22, a distal shaft region 46 (a "third" shaft region in the proximal to distal direction) facing the distal plate portion 24 and a central shaft region 48 (a "second" shaft region in the proximal to distal direction) arranged in between the proximal shaft region 44 and the distal shaft region 46. In another embodiment, the central shaft region 48 may directly be connected to the proximal plate portion 22 and/or the distal plate portion 24 (i.e., without the proximal shaft region 44 and/or the distal shaft region 46 arranged therebetween).

The central shaft region 48 is provided with a plurality of openings 50. The central shaft openings 50 form through-holes extending substantially orthogonal from the upper plate surface 28 to the bone facing plate surface 30 of the femur plate 10. In the embodiment of the femur plate 10 shown in FIGS. 1A to 1C, the central shaft openings 50 are arranged in a staggered manner along the center line 20. In particular, no two central shaft openings 50 lie on a (imagined) central shaft line (indicated by the dashed lines 52 in FIG. 1A) intersecting the center line 20 at an angle of approximately 90°. Instead, the plurality of central shaft openings 50 are alternately arranged, or staggered, on the opposing sides of the center line 20 along the longitudinal extension of the central shaft region 48.

As can be best seen in FIG. 1A, the central shaft openings 50 in the femur plate 10 according to FIGS. 1A to 1C each have a substantially equal distance to at least one respective adjacent central shaft opening 50 arranged on the same of the opposing sides of the center line 20. Also, the central shaft openings 50 each have a substantially equal distance to at least one respective adjacent central shaft opening 50 arranged on the opposing side of the center line 20. As such, centers of the central shaft openings 50 in the upper plate surface 28 lie on a (imagined) zig-zag line along the longitudinal extension of the femur plate 10.

The femur plate 10 has a substantially constant lateral extension within the central shaft region 48. Further, within the central shaft region 48, a contour of the femur plate 10 on both of the opposing sides of the center line 20 follows a curved (in particular a wavy) line along a longitudinal extension of the femur plate 10. The contour lines on the opposing sides of the center line 20 run approximately parallel to each other.

The central shaft region 48 of the femur plate 10 according to the embodiment shown in FIGS. 1A to 1C has a total of 16 through-holes 50. The through-holes 50 have a circular shape and substantially correspond in size to the opening 32 in the proximal plate portion 22. A femur plate 10 according to another embodiment may have a different number of through-holes 50 in the central shaft region 48 (e.g., between 8 and 12 through-holes 50). Also, further openings that differ in size and/or in shape from the through-holes 50 may be provided in the central shaft region 48 (in addition or as an alternative to the through-holes 50). At least some of the further openings in the central shaft region 48 may run obliquely from the upper plate surface 28 to the bone facing surface 30.

As can be best seen in FIG. 1A, the proximal shaft region 44 and the distal shaft region 46 both have an elongate hole 54 extending along the center line 20. Each elongate hole 54 is arranged in a respective portion of the proximal shaft region 44 and the distal shaft region 46 facing the central shaft region 48. In the embodiment shown in FIGS. 1A to 1C, such elongate holes 54 are provided for receiving means (e.g., bone screws) for movably pre-fixing the femur plate 10 to the femur 12 (see FIGS. 1B and 1C). In particular, in case means for pre-fixing the femur plate 10 are inserted into one of the elongated holes 54, the elongated shape of the elongate holes 54 allows the femur plate 10 to still be displaced along the longitudinal extension of the respective elongate hole 54 prior to being firmly fixed to bone. For example, the elongate holes 54 may have a length of between about 5 mm and about 10 mm and a lateral width of between about 2 mm and about 8 mm.

The proximal shaft region 44 and the distal shaft region 46 according to the embodiment of the femur plate 10 shown in FIGS. 1A to 1C each have a plurality of openings 56 in the respective portion of the proximal shaft region 44 facing the proximal plate portion 22 and of the distal shaft region 46 facing the distal plate portion 24. The openings 56 form through-holes extending obliquely from the upper plate surface 28 to the bone facing plate surface 30 of the femur plate 10.

Specifically, in the embodiment of the femur plate 10 shown in FIGS. 1A to 1C, four openings 56 are provided in the proximal shaft region 44. Two openings 56 in the proximal shaft region 44 each have centers that lie on an imagined transverse line (indicated by dashed lines 58 in FIG. 1A) that runs orthogonal to the center line 20. Thus, in total, the four centers of the through-holes 56 in the proximal shaft region 44 span a rectangle with a central axis that approximately coincides with center line 20. An average distance (e.g., between about 0 mm and about 1.5 mm) of the centers of the through-holes 56 to the center line 20 in the proximal shaft region 44 is larger than an average distance (e.g., between about 5 mm and about 9 mm, such as between about 6.1 mm and about 6.5 mm) of the centers of the central shaft through-holes 50 to the center line 20 in the central shaft region 48 (see FIG. 1A). In the distal shaft region 46, two openings 56 are provided (see FIGS. 1A to 1C). The openings 56 in the distal shaft region 46 are arranged in a row along the center line 20. In particular, the centers of the openings 56 in the distal shaft region 46 lie on the center line 20.

The through-holes 56 according to the embodiment of the femur plate 10 shown in FIGS. 1A to 1C have a circular shape and substantially correspond in size to the opening 32 in the proximal plate portion 22. A femur plate 10 according to a different embodiment may have a different number of through-holes 56 in the proximal shaft region 44 and/or in the distal shaft region 46. Also, openings that differ in size and/or in shape may be provided (in addition or as an alternative to through-holes 56) in the proximal shaft region 44 and/or in the distal shaft region 46. At least some of the openings 56 in the proximal shaft region 44 and/or in the distal shaft region 46 may run substantially orthogonal from the upper plate surface 28 to the bone facing surface 30.

The proximal shaft region 44 and the distal shaft region 46 both have an additional opening 60 provided (along the center line 20) between the elongate hole 54 and the two or more through-holes 56. In the embodiment shown in FIGS.

1A to 1C, that opening 60 is a fixation opening adapted to receive guidance means to apply to the femur 12 (e.g., to receive a drill guide). In another embodiment, only one of the proximal shaft region 44 and the distal shaft region 46 may have the elongate hole 54 and/or the guidance opening 60. Moreover, additional openings may be provided along the center line 20 or on opposing sides thereof in the femur plate 10.

In general, the through-holes 32, 40, 50, 56 in the femur plate 10 according to the embodiment shown in FIGS. 1A to 1C are configured to receive locking bone screws and non-locking bone screws (e.g., compression or cortical screws). In another embodiment, for example, only the through-holes 32, 40 in the proximal plate portion 22 and/or the distal plate portion 24 are configured to receive locking bone screws. At least in this case, the through-holes 50, 56 in the shaft portion 26 may be configured to receive non-locking bone screws (e.g., compression or cortical screws) or different bone fasteners (e.g., bone pegs having rod-like or pin-like shafts).

The proximal plate portion 22 of the femur plate 10 is anatomically pre-formed to conform to the trochanter region 14 of the femur 12. In particular, the proximal plate portion 22 in an implanted state conforms to the convex surface of the femur 12 in the region of the greater trochanter. Also, the distal plate portion 24 is anatomically pre-formed to conform to the condyle region 16, in particular the convex surface of the femur 12 in the region of the medial condyle. As such, the femur plate 10 provides conformity both proximally in the trochanter region 14 and distally in the condyle region 16 of the femur 12, without requiring intense contouring when fixing the femur plate 10 to the femur 12.

As can be best seen from FIG. 1C, the proximal plate portion 22 extends upwardly in a vertical direction from the bone facing surface 30 to the upper plate surface 28 of the femur plate 10. A respective angle between the longitudinal axis of the proximal plate portion 22 and a longitudinal axis of the proximal shaft region 44 of the shaft portion 26 (see FIG. 1A) is determined based on average dimensions and shapes of the shaft region 18 and the trochanter region 14 of the human femur 12. For example, angles between about 19° and about 24° may be provided. Also, the (above described) lateral angle between the longitudinal axis 38 of the distal plate portion 24 and the longitudinal axis of the shaft portion 26 (see FIG. 1A) is determined based on average dimensions and shapes of the condyle region 16 and the shaft region 18 of the human femur 12.

As can be gathered from FIG. 1C, the shaft portion 26 of the femur plate 10 according to the embodiment shown in FIGS. 1A to 1C is convexly shaped along its lateral extension (so as to conform to the diaphysis and metaphysis regions of the femur 12). In a shaft portion 26 according to another embodiment, a number of openings (especially through-holes 56 in the proximal shaft region 44, through-holes 52 in the central shaft region 48 and/or through-holes 56 in the distal shaft region 46) may vary dependent on the length of the human femur 12, such as the diaphysis and metaphysis regions.

Figure 2A:
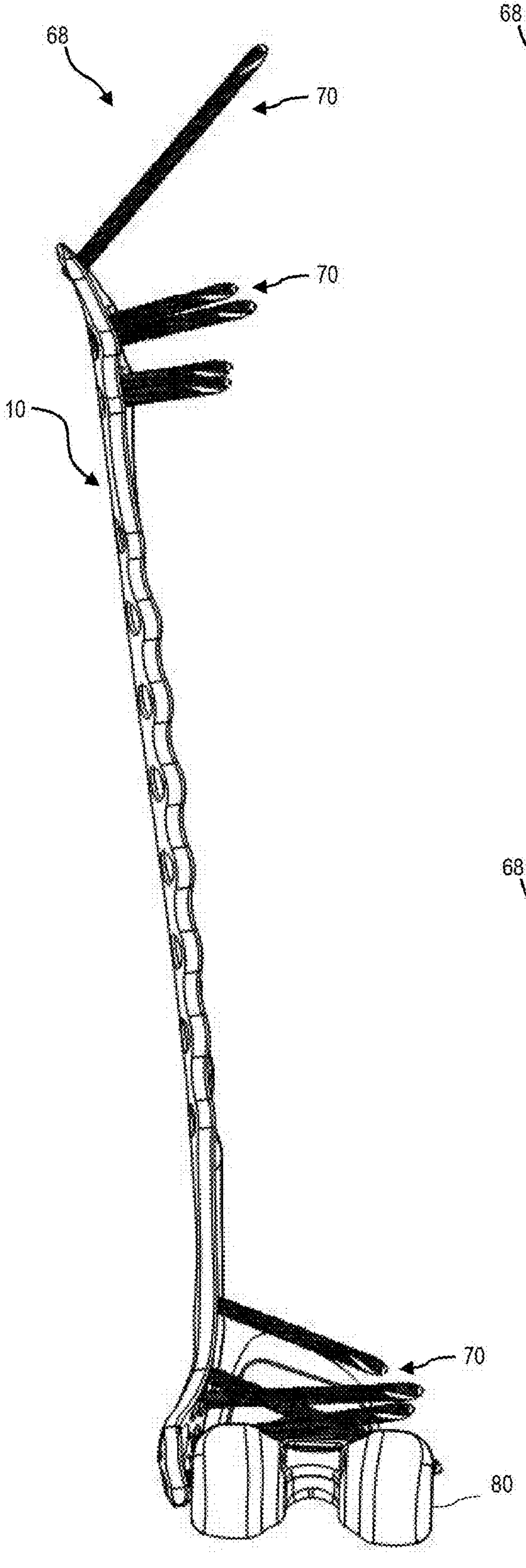
FIG. 2A-2E show perspective views of a periprosthetic implant system including a femur plate according to the first embodiment.
Figure 2B:
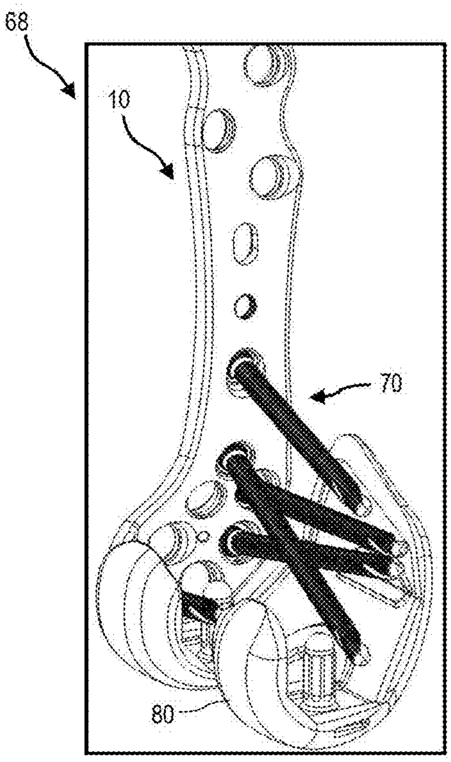
Figure 2C:
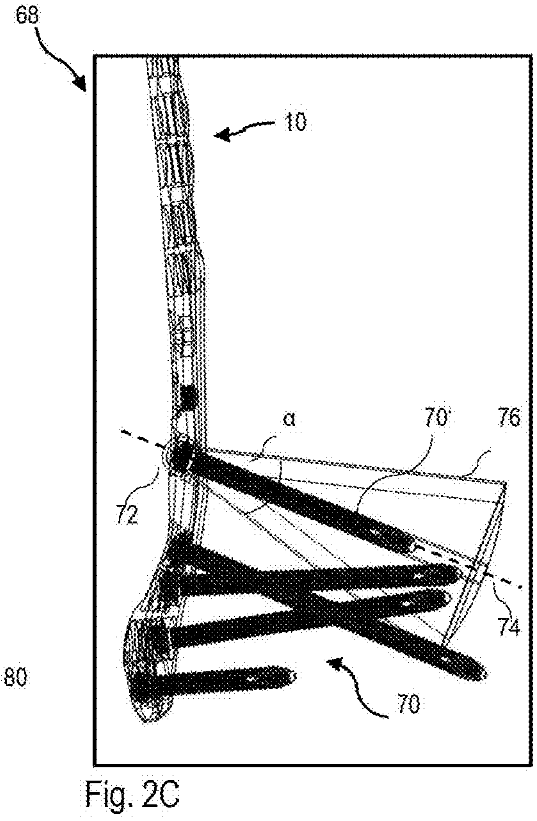
Figure 2D:
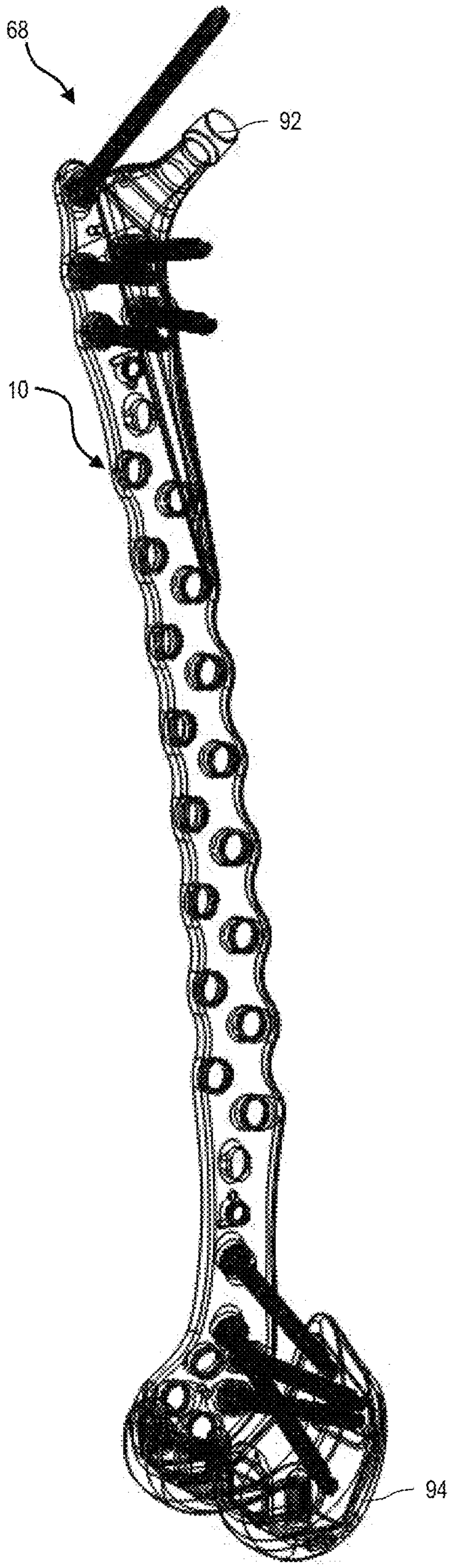
Figure 2E:
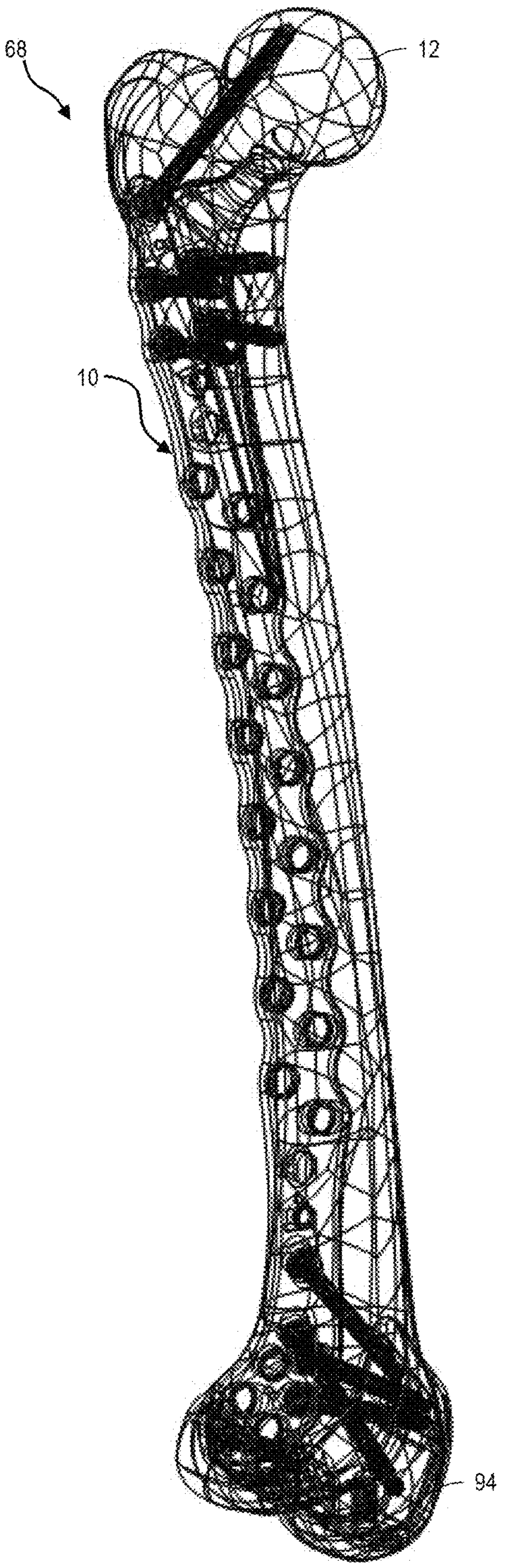

FIGS. 2A to 2E show perspective views of a periprosthetic implant system, generally denoted as 68, comprising the femur plate 10 and bone fasteners, generally denoted by 70, inserted through some of the openings in the femur plate 10 to attach the femur plate 10 to the femur 12 (see FIG. 2E). In particular, bone fasteners 70 for bi-cortical fixation are inserted through the openings in the proximal plate portion 22 (i.e. into the proximal plate through-hole 32, see FIG. 1A) and the proximal shaft region 44 (i.e., the through-holes 56) for insertion into at least a neck of the femur 12 (see FIGS. 1C and 2E). Moreover, bone fasteners 70 for bi-cortical fixation are inserted through the openings in the distal shaft region 46 (i.e. through-holes 56) and the distal plate portion 24 (through-holes 40) for insertion into the medial condyle of the femur 12 (see FIGS. 1C and 2E).

In the embodiment of the periprosthetic implant system 68 shown in FIGS. 2A to 2E, the bone fasteners 70 are locking bone screws or non-locking bone screws that lockingly (or non-lockingly) engage with a (not-shown) locking structure provided in the openings. The locking structure, for example, includes a circumferential lip adapted to engage with a self-cutting portion of the inserted bone screws 70. In an alternative implementation, the locking structure may include a threaded portion or the locking structure may have one or more protrusions extending in a radial direction into the openings. In another embodiment of the periprosthetic implant system 68, bone fasteners 70 for mono-cortical fixation may be inserted through at least some of the openings in the femur plate 10 (see FIGS. 1A to 2E).

At least some of the openings in the femur plate 10 (see FIGS. 1A to 2E) allow for polyaxial insertion of the bone fasteners 70. In particular, as can be exemplarily gathered from FIG. 2C, the bone fastener 70' and the plate opening 72 in this case engage such that the bone fastener 70' is inserted into the femur 12 (see FIGS. 1B and 1C) in prolongation of the opening's 72 vertical axis (indicated by the dashed line 74 shown in FIG. 2C) or along any axis within a cone 76 around the openings vertical axis 74. For example, the cone 76 has an opening angle $\alpha$ of between about 30° and about 40°. Alternatively, smaller opening angles down to about 10° or larger opening angles up to about 50° may be provided.

With regard to the femur plate 10 shown in FIGS. 2A to 2E, polyaxial insertion of the bone fasteners 70 is provided by the through-holes 32, 40, 56 in the proximal plate portion 22, the distal plate portion 24, the proximal shaft region 44 and the distal shaft region 46. In particular, bone screws inserted polyaxially into the through-holes 56 in the distal shaft region 46 have the function of kick-stand screws. In another embodiment of the femur plate 10, at least some of the through-holes 32, 40, 56 in the proximal plate portion 22, the distal plate portion 24, the proximal shaft region 44 and/or the distal shaft region 46 may be adapted for mono-axial insertion of bone fasteners 70. Also, openings (e.g., through-holes 50) in the central shaft region 48 may at least partially be adapted for polyaxial insertion of bone fasteners 70.

As can be seen in FIGS. 2A, 2B, 2D and 2E, the periprosthetic implant system 68 comprises at least one implant, such as a hip prosthesis 92 implanted in the trochanter region 14 of the femur 12 (see FIGS. 2D and 2E), a knee prosthesis 94 implanted in the condyle region 16 of the femur 12 (see FIGS. 2A, 2B, 2D and 2E) or a (not-shown) intramedullary nail.

In the embodiment of the periprosthetic implant system 68 shown in FIGS. 2A to 2E, the opening angles $\alpha$ of the insertion cones 76 (see FIG. 2C) of femur plate 10 openings are selected such that none of the inserted bone fasteners 70 touches an implant 92, 94 in its implanted state. In another embodiment, plate openings in the femur plate 10 (see FIGS. 1A to 2E) may be provided to define a cone 76 (see FIG. 2C) with an opening angle $\alpha$ that allows a bone fastener 70 inserted through the opening to push an implant (such as the hip prosthesis 92 or the knee prosthesis 94) in a desired position. In each case, the femur plate 10 and the additional implant (such as the hip prosthesis 92 or the knee prosthesis 94) have to be jointly dimensioned to achieve the desired effect of intentionally preventing touching of the implant by the bone fasteners 70 or intentionally enabling a pushing of the implant via at least one of the bone fasteners 70.

Figure 3A:
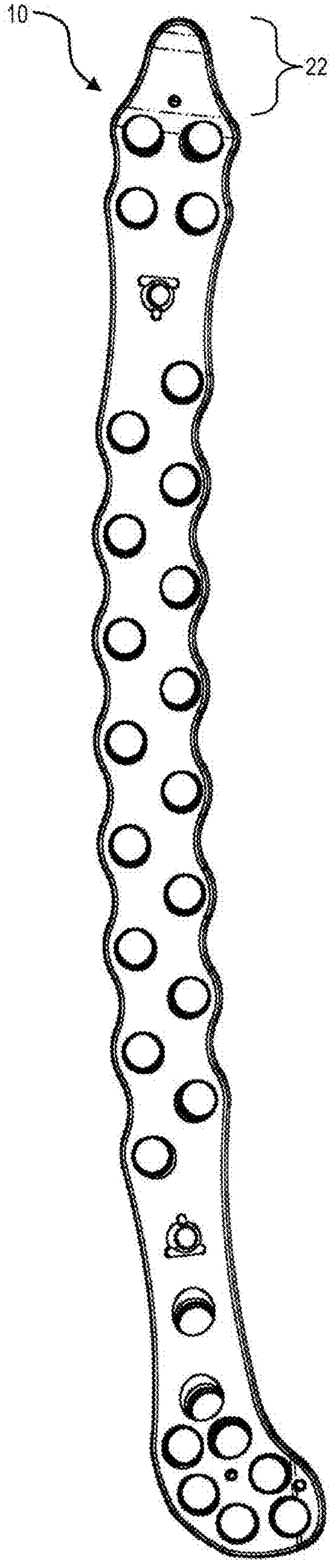
FIGS. 3A-3C show perspective views of femur plates according to a second, a third and a fourth embodiment.
Figure 3B:
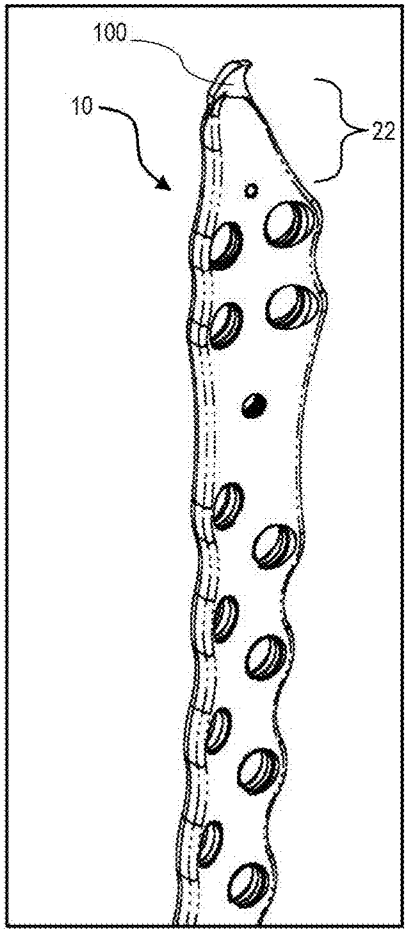
Figure 3C:
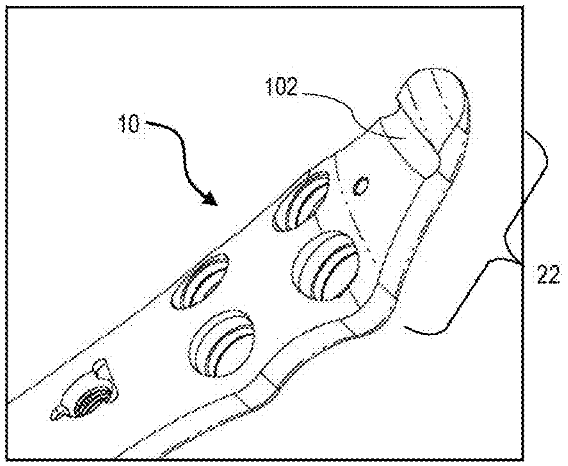

FIGS. 3A to 3C show different further embodiments of the femur plate 10. Since the femur plates 10 shown in FIGS. 3A to 3C are similar to the femur plate 10 shown in FIGS. 1A to 2E in most aspects, only differences between the embodiments are discussed in the following.

To start with, the proximal plate portion 22 of the femur plates 10 according to FIGS. 3A to 3C does not comprise any opening (such as the proximal plate through-hole 32, see FIG. 1A). Moreover, the shaft portion 26 of the femur plates 10 according to FIGS. 3A to 3C does not comprise the elongate holes 54 (see FIG. 1A).

The proximal plate portion 22 of the femur plate 10 according to the embodiment shown in FIG. 3B comprises a hook 100 for insertion into bone of the trochanter region 14 of the femur 12 (see FIGS. 1B and 1C). The hook 100 is formed as a convexly curved proximal extension of the proximal plate portion 22. In particular, the hook extends from the tip 34 of the proximal plate portion 22 in a vertical direction from the upper plate surface 28 to the bone facing surface 30 (see FIG. 1C). In an alternative to the hook 100, a (not-shown) spike for insertion into the trochanter region 14 may be disposed on the bone facing surface 30 of the proximal plate portion 22.

The proximal plate portion 22 of the femur plate 10 according to the embodiment shown in FIG. 3C comprises a channel 102 configured to receive a (not-shown) surgical cable. The channel 102 is formed as an elongated recess (e.g., a groove) that extends perpendicularly to the longitudinal extension of the proximal plate portion 22. The channel 102 according to FIG. 3C is formed on the upper plate surface 28 of the femur plate 10 with an open side that faces away from the femur. Accordingly, the channel 102 allows the proximal plate portion 22 of the femur plate 10 to be fixed to the trochanter region 14 of the femur 12 (see FIGS. 1B and 1C) by means of the surgical cable. When the surgical cable runs through the channel 102, an undesired change in position of the surgical cable along the proximal portion 22 can be avoided (e.g., upon being fastened or thereafter).

In another embodiment, an alternative or additional channel may be formed on the bone facing surface 30 to receive a surgical cable for fixation of an additional bone plate (e.g., to an opposite femur side). Further, the proximal plate portion 22 according to FIG. 3C may have additional channels (e.g., extending in parallel to channel 102) or may have the hook 100 or the spike as described with regard to the embodiment shown in FIG. 3B. Also, the hook 100 according to FIG. 3B and/or the (at least one) channel 102 according to FIG. 3C may be comprised by the femur plate 10 shown in FIGS. 1A to 2E (i.e., including the through-hole 32 in the proximal plate portion 22).

Figure 4:
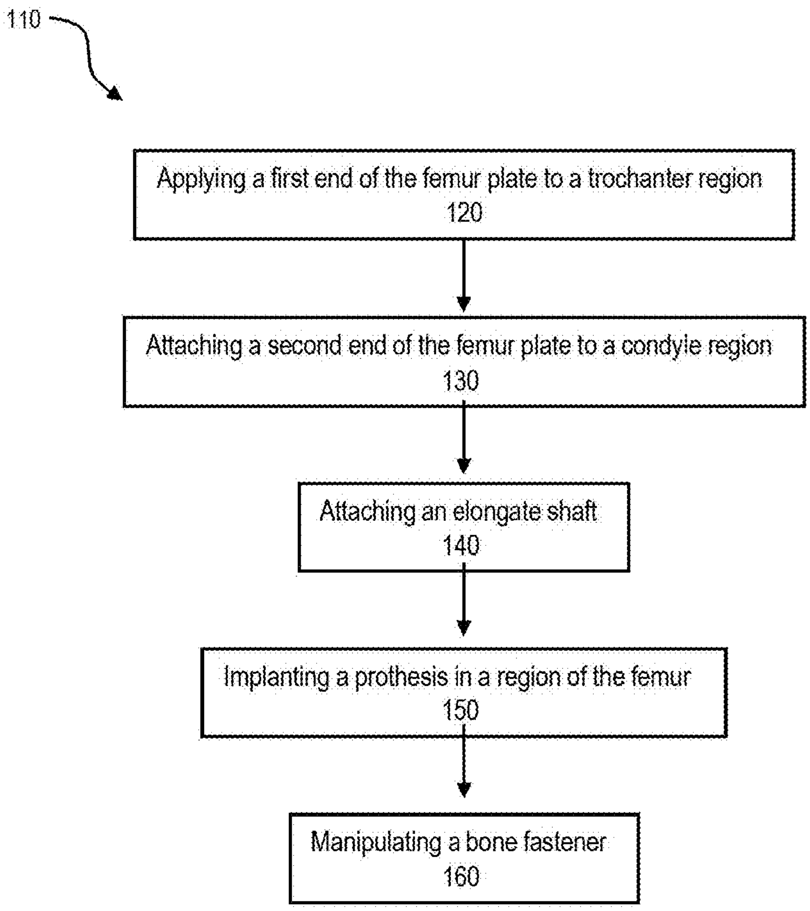
FIG. 4 shows a flow diagram of a method of implanting a femur plate according to the above embodiments.

FIG. 4 shows an exemplary flow diagram 110 of a method of implanting a femur plate 10, such as one of the femur plates 10 described with regard to the embodiments shown in FIGS. 1A to 3C.

In step 120, a first end portion (e.g., the proximal plate portion 22 shown in FIGS. 1A to 3C) of the femur plate 10 is applied to a trochanter region 14 of the femur 12 (see FIGS. 1B and 1C). With regard to the embodiment of the femur plate 10 shown in FIGS. 1A to 2E, this step 120 of applying the first end portion includes attaching that first end portion to the trochanter region 14 by inserting a bone fastener 70 through an opening (i.e., the proximal plate through-hole 32) in the first end portion.

In addition, or as an alternative, step 120 of applying the first end portion to the trochanter region includes inserting a hook 100 (see FIG. 3B) into the trochanter region 14 of the femur 12 and/or attaching the first end portion of the femur plate 10 by means of a surgical cable (as described with regard to the embodiment of the femur plate 10 shown in FIG. 3C).

The method further comprises a step 130 of attaching a second end portion (e.g., the distal plate portion 24 shown in FIGS. 1A to 3C) of the femur plate 10 to a condyle region 16 of the femur 12 (see FIGS. 1B and 1C) by inserting a bone fastener 70 through at least one opening (e.g., the distal plate through-holes 40) in the second end portion.

Moreover, the method comprises a step 140 of attaching an elongate shaft (e.g., the shaft portion 26 of the femur plate 10 according to FIGS. 1A to 3C) to a shaft region 18 of the femur 12 (see FIGS. 1B and 1C) by inserting a bone fastener 70 through an opening (e.g., the central shaft through-holes 50) in the elongate shaft.

Steps 120 to 140 can generally be performed in the indicated order or in a different order.

In the shown example, the method further comprises a step 150 of implanting at least one prosthesis (e.g., hip prosthesis 94 or knee prosthesis 92, see FIGS. 2A, 2B, 2D and 2E) in a region of the femur 12 and a step 160 of manipulating one or a plurality of the inserted bone fasteners 70 when inserted through an associated opening in the femur plate 10. By manipulating the bone fasteners 70 such that these bone fasteners 70 touch the implanted prosthesis 92, 94, the implanted prosthesis 92, 94 can be pushed into a desired position, in particular an anatomic position. In another example of the method 110, at least some of the bone fasteners 70 are inserted such that these bone fasteners 70 do not touch the implanted prosthesis 92, 94. Step 150 could also be performed before steps 120 to 140.

As has become apparent from the above embodiments, the femur plate described herein can be used either alone or in combination with one or more additional implants. The femur plate provides fixation over the diaphysis region and both, proximally in the trochanter region and distally in the condyle region of the femur. In view of the anatomically pre-formed regions of the femur plate, no (or no significant further) contouring for appropriate fixation to the femur to be treated is needed. The femur plate can also be used in periprosthetic scenarios with one or more prostheses in the femur (such as a hip prosthesis, knee prosthesis or intramedullary nail).

The features described in relation to the exemplary embodiments shown in the drawings can be readily combined to result in different embodiments. It is apparent, therefore, that the present disclosure may be varied in many ways. Such variations are not regarded as a departure from the scope of the invention, and all modifications within the scope of the appended claims are included therein.

The invention claimed is:

1. A femur plate configured to project from a trochanter region to a condyle region of a femur, the femur plate comprising:

a bone facing surface and an upper surface opposite the bone facing surface;

at least one first opening configured to receive a bone fastener for attachment of the femur plate to the condyle region;

a plurality of second openings configured to receive a bone fastener for attachment of the femur plate to a shaft region of the femur; and an elongated shaft portion extending along a center line and comprising the plurality of second openings, wherein:

the elongated shaft portion is convexly shaped along its lateral extension to conform to the shaft region of the femur, the elongated shaft portion comprises a proximal shaft region, a central shaft region with multiple of the plurality of second openings, and a distal shaft region, at least one of the proximal shaft region of the elongated shaft or the distal shaft region of the elongated shaft comprises an elongated hole extending along the center line, the elongated hole being configured to receive a bone fastener for movably pre-fixing the femur plate to the femur, a first end of the femur plate comprises a tapering tip that extends in a direction away from the bone facing surface and towards the upper surface, and the first end of the femur plate conforms to the trochanter region.

2. The femur plate of claim 1 further comprising a first end portion and a second end portion, wherein:

the elongate shaft portion extends from the first end portion to the second end portion, the first end portion is anatomically pre-formed to conform to a convex surface of a greater trochanter of a femur, and the second end portion is anatomically pre-formed to conform to a convex surface of a lateral condyle of the femur.

3. The femur plate of claim 2, wherein the first end portion comprises at least one channel configured to receive a surgical cable, wherein the at least one channel extends generally perpendicularly to a longitudinal extension of the first end portion.

4. The femur plate of claim 2, wherein multiple first openings are arranged in the second end portion of the femur plate to each receive a bone fastener for insertion into a medial condyle.

5. The femur plate of claim 2, wherein centers of two second openings in the first end portion lie on opposing sides of the center line.

6. The femur plate of claim 5, wherein the second openings in the first end portion are arranged to receive bone fasteners for bi-cortical fixation.

7. The femur plate of claim 5, wherein the centers of the two second openings in the first end portion lie on a first line intersecting the center line at an angle of approximately 90°.

8. The femur plate of claim 5, wherein a first shaft region comprises four second openings having centers that define a rectangle that is intersected by the center line.

9. The femur plate of claim 2, wherein centers of two second openings in a second end portion lie on opposing sides of the center line.

10. The femur plate of claim 9, wherein the second openings in the second end portion are arranged to receive bone fasteners for at least one of mono-cortical and bi-cortical fixation.

11. The femur plate of claim 9, wherein no two second openings in the second end portion-on opposing sides of center line of a second shaft region have their centers on a second line intersecting the center line at an angle of approximately 90°.

12. The femur plate of claim 1, wherein no elongated hole is arranged within the central shaft region.

13. The femur plate of claim 1, wherein at least one third opening is arranged in a first end of the femur plate to receive a bone fastener for insertion into a femur neck.

14. The femur plate of claim 13, wherein at least one of:

the at least one first opening, the at least one third opening, or at least one of the plurality of second openings comprises a locking structure for locking a bone fastener received through that opening at a selected angle to the femur plate.

15. The femur plate of claim 1, wherein at least one third opening is centrally located in the tapering tip.

16. The femur plate of claim 1, wherein a first end of the femur plate comprises a hook or spike configured to be inserted into trochanter bone.

17. The femur plate of claim 1, wherein a second end of the femur plate is club-shaped and angled laterally relative to a longitudinal extension of the elongate shaft portion towards a medial condyle.

18. The femur plate of claim 1, further comprising a first side surface extending between the bone facing surface and the upper surface and a second side surface opposite the first side surface and extending between the bone facing surface and the upper surface, wherein:

the tapering tip is defined by the first side surface and the second side surface, and the tapering tip enlarges distally towards the elongated shaft region from a proximal tip of the femur plate.

19. A periprosthetic implant system comprising:

at least one implant configured to be implanted in a region of one of a trochanter and a condyle of a femur; and a femur plate comprising:

a bone facing surface and an upper surface opposite the bone facing surface;

at least one first opening configured to receive a bone fastener for attachment of the femur plate to the condyle region;

a plurality of second openings configured to receive a bone fastener for attachment of the femur plate to a shaft region of the femur; and an elongated shaft portion extending along a center line and comprising the plurality of second openings, wherein:

the elongated shaft portion is convexly shaped along its lateral extension to conform to the shaft region of the femur, the elongated shaft portion comprises a proximal shaft region, a central shaft region with multiple of the plurality of second openings, and a distal shaft region, at least one of the proximal shaft region of the elongated shaft and the distal shaft region of the elongated shaft comprises an elongated hole extending along the center line, the elongated hole being configured to receive a bone fastener for movably pre-fixing the femur plate to the femur, a first end of the femur plate comprises a tapering tip that extends in a direction away from the bone facing surface and towards the bone facing surface, and the first end of the femur plate conforms to the trochanter region.

20. The implant system of claim 19, wherein the femur plate further comprises a first end portion and a second end portion, wherein:

the elongate shaft portion extends from the first end portion to the second end portion, the first end portion is anatomically pre-formed to conform to a convex surface of a greater trochanter of a femur, and the second end portion is anatomically pre-formed to conform to a convex surface of a lateral condyle of the femur.

21. The implant system of claim 19, wherein no elongated hole is arranged within the central shaft region.

22. The implant system of claim 19, wherein the femur plate further comprises at least one third opening is arranged in a first end of the femur plate to receive a bone fastener for insertion into a femur neck.

23. The implant system of claim 22, wherein the at least one third opening of the femur plate is arranged in the femur plate such that a bone fastener inserted through that opening does not touch the implant in its implanted state.

24. The implant system of claim 22, wherein at least one of:

the at least one first opening, at least one of the plurality of second openings, or the at least one third opening comprises a locking structure for locking a bone fastener received through that opening at a selected angle to the femur plate, and wherein selectable angles for a particular plate opening define a cone that does not touch the implant in its implanted state.

* * * * *